United States Patent [19]

Armitage

[11] 4,269,199
[45] May 26, 1981

[54] INDUCING LOCAL HYPERTHERMIA BY INDUCTIVE DIATHERMY

[75] Inventor: David Armitage, Bangor, Wales
[73] Assignee: Harry H. Leveen, Charleston, S.C.
[21] Appl. No.: 20,356
[22] Filed: Mar. 14, 1979
[51] Int. Cl.³ .............................................. A61N 1/40
[52] U.S. Cl. ................................................. 128/804
[58] Field of Search .................... 128/1.3, 1.5, 419 R, 128/420 R, 420 A, 421, 422, 423 R, 783, 804

[56] References Cited

U.S. PATENT DOCUMENTS

| 3,991,770 | 11/1976 | LeVeen | 128/804 |
| 4,186,729 | 2/1980 | Hamison | 128/1.3 |

FOREIGN PATENT DOCUMENTS

| 718637 | 2/1942 | Fed. Rep. of Germany | 128/804 |
| 807349 | 1/1937 | France | 128/804 |
| 1045546 | 10/1966 | United Kingdom | 128/804 |

Primary Examiner—Lee S. Cohen
Attorney, Agent, or Firm—Brooks, Haidt, Haffner & Delahunty

[57] ABSTRACT

A method for inducing local hyperthermia in treatment of a tumor by short wave diathermy which involves moving an induction coil over the portion of the body containing the tumor such that the axis of the coil constantly transects different portions of the tumor.

5 Claims, 5 Drawing Figures

INDUCING LOCAL HYPERTHERMIA BY INDUCTIVE DIATHERMY

This invention relates to inducing local hyperthermia by short wave diathermy utilizing an induction coil and, in particular, provides a method of manipulating a coil to maximize absorption of energy in a predetermined zone of treatment within the body.

Recently it has been found that short wave diathermy (thermotherapy) can be utilized in the treatment of tumors (LeVeen U.S. Pat. No. 3,991,770). This treatment is predicated on the perception that blood flow in tumors is poor, and hence the tumor can be selectively heated to the point of destruction by utilizing relatively high power, short wave diathermy without damage to adjacent normal tissue, as the blood flow through the adjacent normal tissue cools the tissue at a faster rate than the slower blood flow through the tumor. In the treatment of tumors the diathermy unit is generally of higher power than used in conventional diathermy treatment and typically is on the order of up to 2 Kw.

When an induction coil is used as a means of inducing local hyperthermia in a patient, deep penetration and generalized warming in the vicinity of the induction coil is experienced by the patient. It has now been found, however, that the absorption of energy is non-uniform and a distinct dead zone more or less coincident with the axis of the coil exists. This is particularly so when a flat (pancake) coil is employed having relatively few (one or two) turns. While in conventional diathermy the existence of this dead zone is of no particular consequence, as blood flow readily carries heat through the area under treatment such that a generalized feeling of warmth is experienced, when inductive short wave diathermy is employed to induce local hyperthermia in the treatment of tumors, the poor supply of blood to the tumor can result in preventing selective heating of the tumor.

It is therefore a principal object of this invention to provide a technique for using inductive short wave diathermy in the treatment of tumors to maximize absorption of radio frequency electromagnetic energy in the tumor.

In accordance with this invention a coil is positioned with its axis transecting the portion of the body containing the tumor, the coil is then moved while energized with radio frequency electrical energy through a path which is generally in a direction normal to the axis of the coil and which is repeated such that the axis of the coil constantly transects different portions of the tumor, or of the body closely adjacent to the tumor. Where a flat coil is employed, the path of movement is preferably generally coplanar with the coil. Where a single turn coil is employed the path of movement preferably is reciprocating or orbital having an excursion approximating that of the diameter of the coil centered over the center of the tumor to be treated. Where the tumor is of ovoid shape an elliptical path of movement may be indicated. The path of movement of the coil should be repetitious, as the body acts as a low pass filter, and it is necessary to repeat movement fast enough to obtain a summation of heating effect. In other words the coil should repetitively be in the same position in not less than five seconds and preferably more rapidly.

For a more complete understanding of the practical application of the principles of this invention reference is made to the appended drawings in which.

Figure 1:
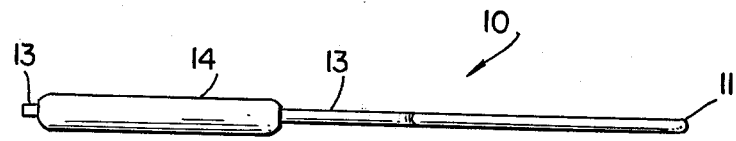
FIG. 1 is a side view of a single turn pancake induction coil.
Figure 2:
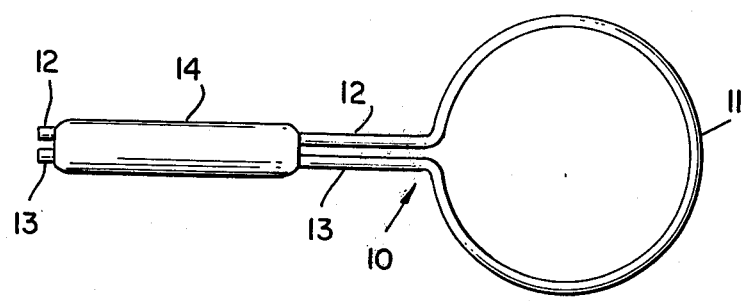
FIG. 2 is a plan view of the induction coil shown in FIG. 1.

Referring more particularly to FIGS. 1 and 2 there is illustrated an induction coil applicator which is generally indicated by the reference numeral 10. Coil 10 includes a single turn, i.e., a loop 11 of copper tubing which forms almost a complete circle with the ends 12 and 13 of the tubing turned into parallel relationship in the plane of loop 11 extending away from the loop 11. An insulated handle 14 is mounted over ends 12 and 13 to permit manipulation of coil 10. Ends 12 and 13 are brought through handle 14 and in usage are connected to flexible, non-conductive tubing for the purpose of permitting cooling water to be flowed through coil 10 and are connected to a suitable radio frequency generator and parallel tuning capacitor. Preferably coil 10 is also provided with a grounded electrostatic shield as described in copending application, Ser. No. 20,357, filed Mar. 14, 1979 by David Armitage, entitled ELECTROSTATIC SHIELD.

Figure 4:
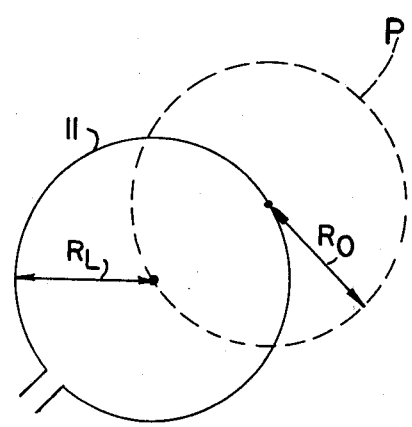
FIG. 4 is a diagram indicating movement utilized to obtain the curves in FIG. 3.

In carrying out manipulation of coil 10 in accordance with this invention, coil 10 is placed with loop 11 generally parallel to and close to the surface of the body containing the tumor to be treated, generally such that a line normal to the center of loop 11 (the axis of loop 11) transects the location of the tumor. Coil 10 is then moved utilizing handle 14 to carry loop 11 in a path coplanar with loop 11. This is illustrated in FIG. 4 where the reference numeral P denotes a path of movement. In a simple case path P can be circular, however, spiral paths which were repeated in and out, elliptical paths and irregular paths all can be employed, the important factor being to keep moving the loop in a path overlying the tumor, as close to the surface of the body containing the tumor as is convenient. Treatment is carried out with intensity of radio frequency energy and for a duration sufficient to produce necrosis of the underlying tumor. The frequencies preferred are 13.56 MHz and 27.12 MHz; however, these particular frequencies are selected only because they are the lower frequencies available pursuant to government regulation and are not critical.

Figure 5:
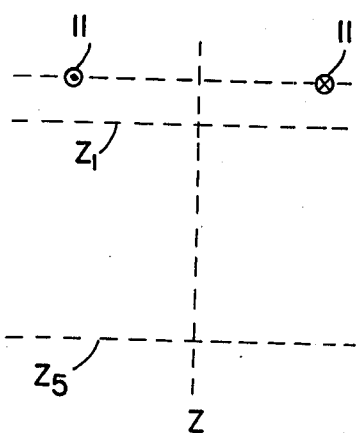
FIG. 5 is a sketch related to the generation of curves shown in FIG. 3.
Figure 3:
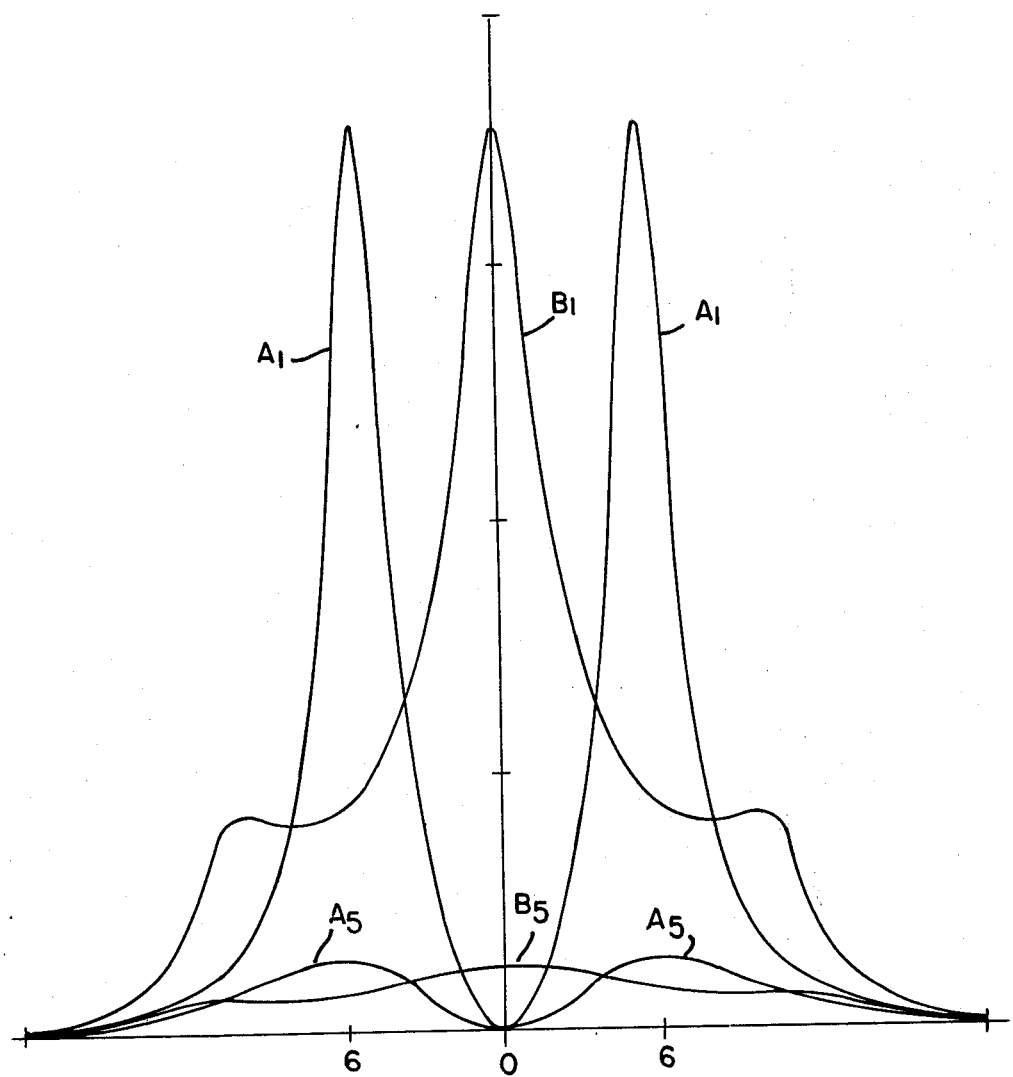
FIG. 3 is a series of curves depicting energy absorption under different circumstances.

FIG. 3 is a group of curves illustrating the principles of this invention. In FIG. 3 the curves were developed with reference to a circular loop 11 having a radius, $R_L$, of 6 centimeters. FIG. 3 shows power absorption in planes parallel to the loop which are spaced 1 centimeter and 5 centimeters from loop 11, as shown in FIG. 5, these planes being denoted by the references numerals $Z_1$ and $Z_5$, respectively. Curves $A_1$ and $A_5$ show power absorption in planes $Z_1$ and $Z_5$, respectively, plotted against the same arbitrary scale, as an ordinate, and plotted against distance from the axial line through the coil in centimeters, as the abissa, when loop 11 is stationary. As will be seen in FIG. 3 when the coil remains stationary, power absorption is null on the axis through loop 11, and approaches a maximum at the radial distance of loop 11 from the axis.

Loop 11 is then moved through an orbital path, indicated in FIG. 4 in which the radius of orbital movement $R_0$, is equal to $R_L$ (6 centimeters). Absorption again is plotted as an ordinate utilizing the same arbitrary scale, and absorption is measured from the center of path P in planes $Z_1$ and $Z_5$. The results are shown in curves $B_1$ and $B_5$, respectively. It will be seen that when loop 11 is orbited through a circular path having a radius equal to that of loop 11 absorption peaks on the axis of rotation.

Other curves have been made which indicate the gradual approach of the two cusps of curves A (when the loop is stationary) as $R_0$ increases until the curves merge, when $R_L = R_0$. The single cusp shown in curves B divides into two cusps as $R_0$ is increased beyond $R_L$ but the dead center found in curves A is not again obtained with $R_0$ as large as $2R_L$.

In practice the size of loop 11 relative to the size of the tumor to be treated and the depth of the tumor below the surface of the skin will determine the preferable orbit for loop 11. The essential thing is that loop 11 must be rapidly moved constantly relative to the tumor in order that the dead spot along the axis of the coil be changed in location relative to the tumor, such that all portions of the tumor are heated. It will be understood that, while reference is made to moving the coil, the body containing the tumor can be moved and the coil held stationary, or both coil and body can be moved to obtain the necessary motion.

I claim:

1. A method for inducing local hyperthermia in treating a tumor with short-wave diathermy which comprises positioning an induction coil with the axis thereof transecting a portion of the body containing the tumor while electrically energizing said coil at a radio frequency, and rapidly moving said coil relative to said body through a repetitive path in a direction approximately normal to said axis of said coil such that said axis of said coil constantly transects different portions of said tumor and the normal tissue adjacent said tumor.

2. The method according to claim 1 in which said path is a closed loop.

3. The method according to claim 2 in which said path is circular.

4. The method according to claim 2 in which said path is reciprocating.

5. The method according to any of claims 1, 2, and 3 in which said coil is a pancake coil and the movement of said coil is coplanar with said coil.

* * * * *